(12) United States Patent
Milton

(10) Patent No.: US 9,498,375 B2
(45) Date of Patent: Nov. 22, 2016

(54) CONTACT LENS TOOL KIT AND METHOD OF USING

(71) Applicant: Invent Horizon, LLC, Raleigh, NC (US)

(72) Inventor: David Timothy Milton, Raleigh, NC (US)

(73) Assignee: Invent Horizon, LLC, Raleigh, NC (US)

(*) Notice: Subject to any disclaimer, the term of this patent is extended or adjusted under 35 U.S.C. 154(b) by 0 days.

(21) Appl. No.: 14/849,489

(22) Filed: Sep. 9, 2015

(65) Prior Publication Data

US 2016/0067085 A1    Mar. 10, 2016

Related U.S. Application Data

(60) Provisional application No. 62/048,176, filed on Sep. 9, 2014.

(51) Int. Cl.
 *A61F 9/00* (2006.01)
(52) U.S. Cl.
 CPC .................... *A61F 9/0061* (2013.01)
(58) Field of Classification Search
 CPC ................ A61F 9/0061; A61F 9/00
 USPC ..................... 294/1.2; 206/5.1; 134/901
 See application file for complete search history.

(56) References Cited

U.S. PATENT DOCUMENTS

| | | | |
|---|---|---|---|
| 3,344,461 A * | 10/1967 | Floor | A45C 11/005 134/901 |
| 5,538,301 A | 7/1996 | Yavitz et al. | |
| 5,695,049 A * | 12/1997 | Bauman | A45C 11/005 206/5.1 |
| 5,732,990 A | 3/1998 | Yavitz et al. | |
| 6,866,462 B2 | 3/2005 | Gilliard | |
| 2002/0063068 A1* | 5/2002 | Faxe | A45C 11/005 206/5.1 |
| 2011/0109107 A1* | 5/2011 | Lin | A61F 9/0061 294/1.2 |

* cited by examiner

*Primary Examiner* — Gabriela Puig
(74) *Attorney, Agent, or Firm* — NK Patent Law, PLLC (57) ABSTRACT

A contact lens tool kit for placement of a contact lens on an eye is provided. The tool kit may include a tool housing for engaging a contact lens tool. The contact lens tool may include an annular groove for selectively engaging a contact lens. The tool kit may also include a lens housing for receiving a contact lens, the lens housing selectively engageable with the tool housing. Engagement of the tool housing and the lens housing permits reception of the contact lens by the contact lens tool. The lens housing may include a plug for draining solution through an aperture of the contact lens tool.

20 Claims, 6 Drawing Sheets

CONTACT LENS TOOL KIT AND METHOD OF USING

CROSS REFERENCE TO RELATED APPLICATIONS

This application claims the benefit of U.S. Provisional Application No. 62/048,176, filed Sep. 9, 2014, which is herein incorporated by reference in its entirety.

TECHNICAL FIELD

The present disclosure relates generally to a contact lens tool and tool kit for engaging a contact lens for placement on an eye. More specifically, the present disclosure relates to a contact lens tool having an annular groove for receiving the contact lens and a tool kit including a lens housing and a tool housing permitting reception of a contact lens by the contact lens tool.

BACKGROUND

Inserting a contact lens can be difficult, for both new users and experienced users alike. Not only is the eye naturally sensitive to touch, but the delicate process of inserting the contact lens properly involves a steep learning curve. It is common for new contact wearers to have several sessions where inserting the contact lens into the eye(s) requires numerous attempts and a significant amount of time. Because of the difficulties associated with inserting contact lenses, many who attempt to use contacts are unsuccessful and may never attempt to wear contacts again.

Another issue common amongst contact lens users is the necessity of making skin-to-lens contact when removing a lens from its storage case and/or when placing the contact lens on the eye. Because fingers may be inserted into the contact lens solution and the contact lens may adhere to the fingers during placement, foreign objects and residue may be introduced into the solution or even directly onto the surface of the contact lens, both of which may result in the objects or residue being introduced to the user's eye, resulting in discomfort or possible infection.

While the technology of the prior art disclose various methods of inserting contact lenses, they fail to teach the ability to easily insert a contact lens into the eye while maintaining sanitary conditions and minimizing the chance that the contact is improperly placed on the eye. Not only is there a risk of introducing foreign matter onto the eye, but inferior placement of the contact lens on the eye could result in air pockets between the contact lens and the eye. Those familiar with wearing contact lenses will appreciate that even minimal errors in the placement of the contact lens on the eye may result in pockets of trapped gas or liquid being formed between the contact lens and the eye during placement.

Notwithstanding the advancements made in the prior art in the field of contact lens storage and use, there remains a need for a contact lens tool kit and tool which improves the ability of a contact lens user to store and use contact lens in a sanitary, easy-to-use manner, while maximizing the chance that each placement of the lens is optimally successful. Disclosed herein are one or more devices and methods that advantageously address these issues.

SUMMARY

This summary is provided to introduce in a simplified form concepts that are further described in the following detailed descriptions. This summary is not intended to identify key features or essential features of the claimed subject matter, nor is it to be construed as limiting the scope of the claimed subject matter.

According to at least one embodiment, a contact lens tool kit is provided. The contact lens tool kit includes a tool housing for engaging a contact lens tool, a lens housing for receiving a contact lens, the lens housing selectively engageable with the tool housing. Engagement of the tool housing and the lens housing permits reception of the contact lens by the contact lens tool.

According to at least one embodiment, a contact lens tool is provided. The contact lens tool includes an annular groove with an outer edge and an interior rise for receiving and positioning the contact lens.

According to at least one embodiment, the contact lens tool includes a hemispherical cavity positioned internally proximal to the groove.

According to at least one embodiment, the contact lens tool includes at least two clefts positioned opposite from each other and extending centrally through the groove to the cavity.

According to at least one embodiment, the contact lens tool includes an aperture extending centrally from the cavity along the length of the contact lens tool to an opening for permitting fluid liquid flow therethrough.

According to at least one embodiment, the contact lens tool includes at least two wings, each extending centrally and away from the interior rise positioned between the clefts for supporting the contact lens, the wings being shaped for contouring the contact tens when inverted.

According to at least one embodiment, an exterior of the capture portion is partially covered by a handle portion coupled thereto.

According to at least one embodiment, the handle portion defines an opening engaged with an aperture extending froth the cavity of the capture portion for permitting fluid flow therethrough.

According to at least one embodiment, engagement of the tool housing with the lens housing is impermeable to fluids.

According to at least one embodiment, the tool housing defines an toot exterior with a tool base positioned on one end of the toot exterior, and the tool base defining a pole extending within the tool exterior for selectively engaging the contact lens toot.

According to at least one embodiment, the tool housing further defines at least one protrusion extending within the tool exterior for supporting the contact lens tool when engaged with the tool housing.

According to at least one embodiment, the lens housing defines a lens base selectively engaged with a plug for releasing fluid therein.

According to at least one embodiment, the lens base defines a plurality of ribs extending centrally within the lens housing for receiving the contact tens.

According to at least one embodiment, the lens housing further defines a ledge extending centrally for supporting engagement of the contact lens tool when the tens housing and tool housing are engaged.

According to at least one embodiment, a method of engaging a contact lens with a contact lens toot is provided. The method includes providing the contact lens tool having a capture portion defining an annular groove for receiving the contact lens, providing a lens housing including a liquid solution and the contact lens therein, inserting the contact lens tool into the lens housing, thereby engaging the contact lens tool with the contact lens and the lens housing.

According to at least one embodiment, the method includes providing a tool housing, wherein the step of inserting the contact lens tool into the lens housing involves engaging the tool housing with the lens housing.

According to at least one embodiment, the method includes disengaging a plug from the lens housing, thereby releasing the liquid solution, and removing the contact lens tool from the lens housing, thereby removing the contact lens engaged to the contact lens tool.

According to at least one embodiment, the method includes disengaging the tool housing from the lens housing such that the contact lens tool remains engaged with the lens housing, disengaging a plug from the lens housing, thereby releasing the liquid solution, and removing the contact lens tool from the lens housing, thereby removing the contact lens engaged to the contact lens tool.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTIONS

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Figure 3:
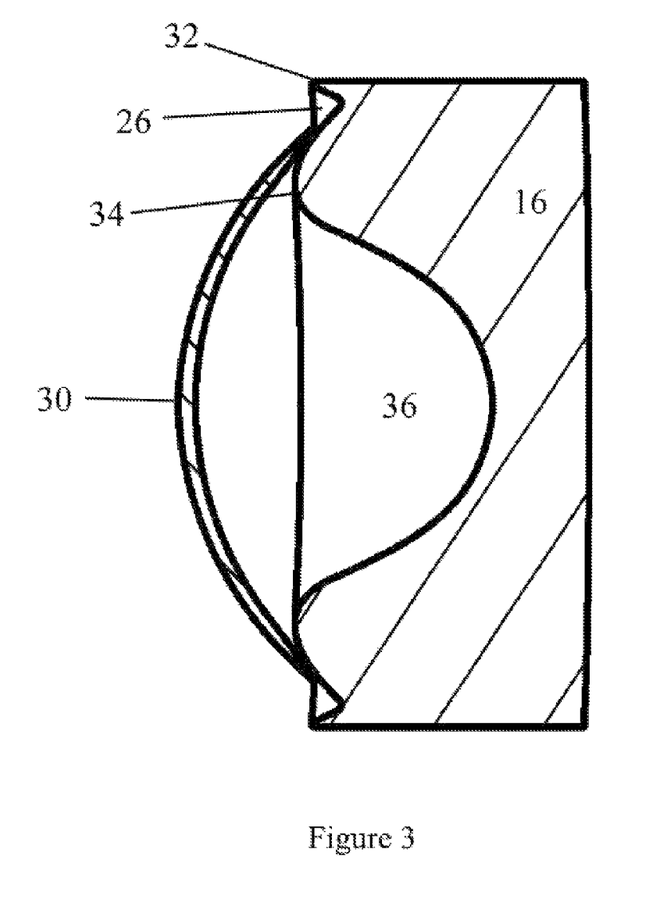
FIG. 3 is cross-section view of the contact lens tool engaged with the contact lens according to one or more embodiments of the present invention.

As will be discussed in more detail infra, this application discloses various embodiments of a contact lens tool kit 10, a contact lens housing 54, a contact lens tool 12, a contact lens tool housing 52 and numerous methods of using these components to aid a contact lens wearer in storing and placing their contact lenses 30. In many embodiments of the present invention, a contact lens 30 is inverted before being placed on the pupil of the wearer's eye, inversion generally meaning that the side of the contact lens 30 that is to directly contact the surface of the eye is convex immediately before being placed, as opposed to being concave when placement is complete. Typically, for a contact tens 30 that has a proper installation direction, the contact lens 30 is concave when the edge of the lens curves inward and convex, or inverted, when the edge flares outward. The methods and components described herein may be applied to either unidirectional or bidirectional contact lenses 30. To reiterate, the inverted contact lens 30 of FIG. 3 is convex, with the surface of the lens 30 to make contact to the eye facing away from the capture portion 16.

By placing a contact lens 30 that is in an inverted form onto the eye, the placement permits the center of the contact lens 30 to make first contact. When the contact lens 30 is being placed on the eye with pressure on the edge of the contact lens 30, contact with the eye causes the contact tens 30 to deform and invert back to its original form, concave. During placement, the contact lens 30 naturally makes additional contact with the eye in a wave-like manner rolling radially outward generally from the center of the contact tens 30. Placing the contact lens 30 on the eye in an inverted manner advantageously permits the contact len's natural placement motion to push gas and liquid from the center of the contact lens 30 out so that no significant pockets of trapped fluids are formed between the contact lens 30 and the eye during the placement. Once the contact lens 30 fully re-inverts to a concave form, the contact lens 30 is then fully placed onto the eye. As will be described infra, according to some embodiments of the present invention, the pressure on the edge of the contact lens 30 may be provided by the capture portion 16 of the contact lens tool 12.

In alternative embodiments of the methods described supra, the contact lens 30 may initially contact the eye using a portion of the contact lens 30 near the edge of the contact lens, such that the way-like motion propagates across the contact, still ensuring that the pockets of trapped fluids, gas or liquid, are minimized.

Figure 1:
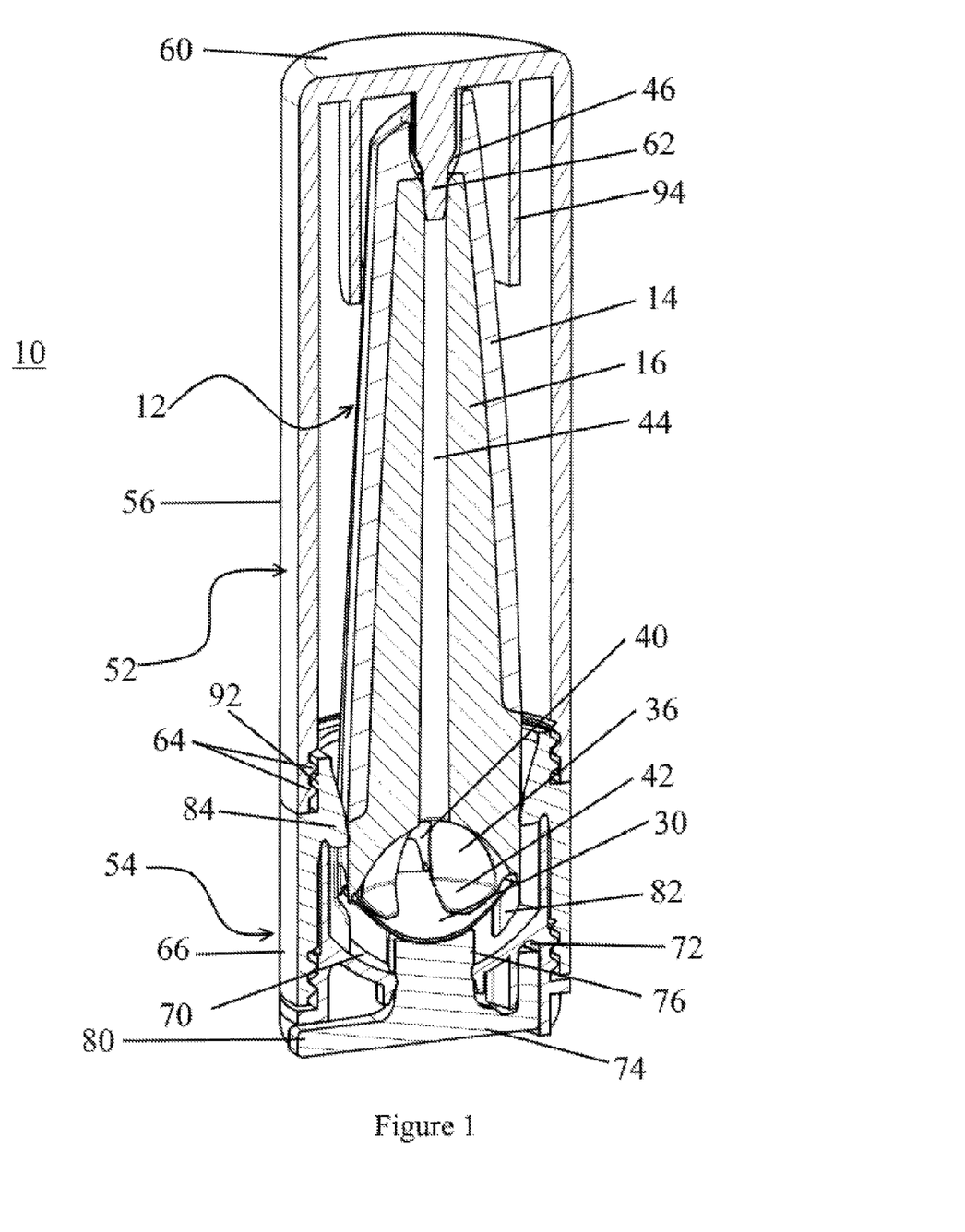
FIG. 1 is a cross-section of the contact lens tool kit according to one or more embodiments of the present invention.

FIG. 1 depicts a contact lens tool kit according to at least one embodiment of this invention. The contact lens tool kit may include a tool housing 52 for housing and/or engaging a contact tens tool 12 and a lens housing 54 for receiving a contact lens 30. The tool housing 52 and lens housing 54 may be selectively engageable with each other. When the tool housing 52 houses the contact lens tool 12 and the lens housing 54 houses a contact lens 30, engagement of the tool housing 52 and the lens housing 54 permits reception of the contact lens 30 by the contact lens tool 12. For example, in one embodiment of this invention, a result of the reception of the contact lens 30 is depicted in FIG. 3B, which depicts the capture portion 16 of the contact lens tool 12 engaging the edge of the contact lens 30. Once the contact lens 30 is received by the contact lens tool 12, insertion of the contact lens 30 into an eye is possible, as described supra.

Figure 2A:
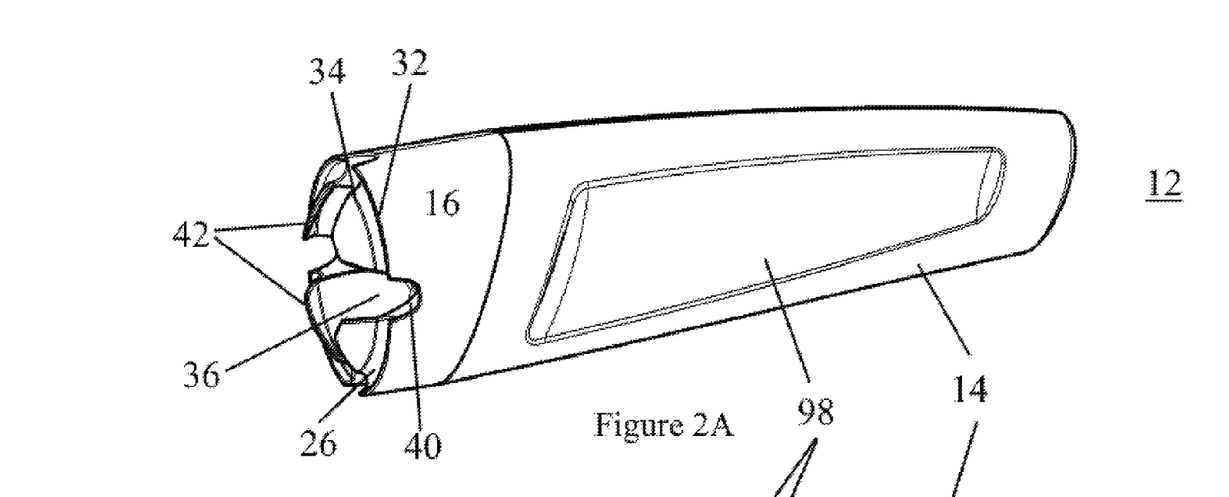
FIG. 2A is a perspective view of the contact lens tool including wings according to one or more embodiments of the present invention.
Figure 2B:
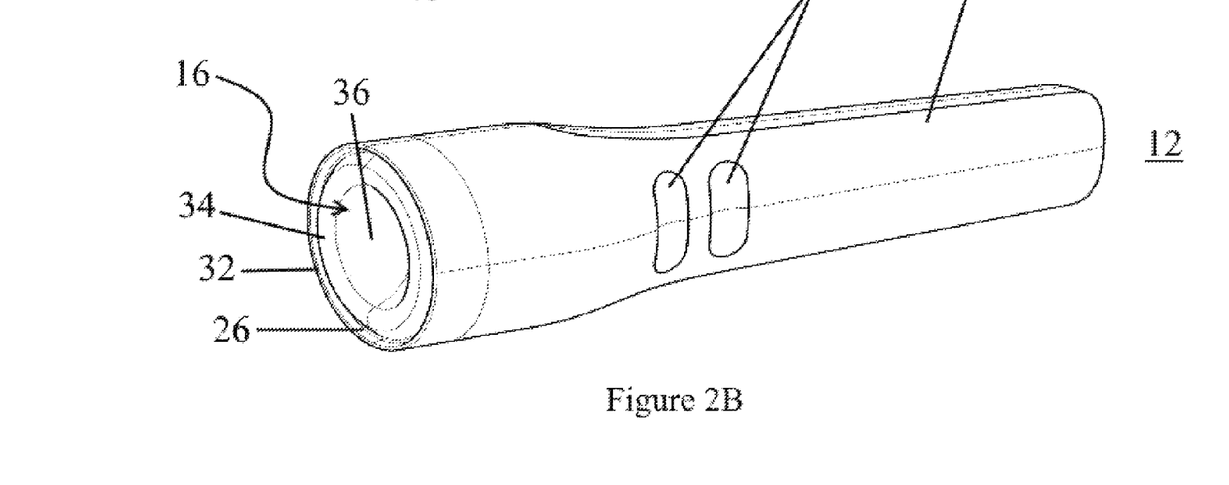
FIG. 2B is a perspective view of the contact lens tool without wings according to one or more embodiments of the present invention.

According to some embodiments, the contact lens tool 12 includes a capture portion 16 for receiving the contact lens 30. FIGS. 2A and 2B depict two embodiments of the capture portion 16, each embodiment depicting the capture portion 16 defining an annular groove 26 with an outer edge 32 for releasably engaging the contact lens 30, as depicted in FIG. 39. The capture portion 16 may also define an interior rise 34 positioned internally of the groove 26 and edge 32. Because an annular groove 26 mirrors the shape of the circular edge of contact tenses 30, engagement of the a contact lens tool 12 having an annular groove 26 is permitted no matter how the annular groove 26 is rotated; any position within a 360 degree rotation about the groove may result in a successful engagement.

Further, as depicted in the embodiments of FIGS. 2A and 2B, the capture portion 16 may define a hemispherical cavity 36 positioned internally proximal to the groove 26. The cavity 36 may be either concave or convex in shape. For example, FIGS. 2A and 2B depict a concave cavity. A convex cavity 36 may help to create additional engagement with the contact lens 30, thereby supporting the contact lens 30 and preventing the contact lens 30 from displacement during engagement and placement, similar to the wing 42 described infra.

The groove 26, edge 32 and/or rise 34 may enable the capture portion 16 of the contact lens tool 12 to engage and hold the contact lens 30 and/or centrally position the contact lens 30 on the tens tool 12. By applying pressure to the edge of the contact lens 30, the contact lens tool 12 enables performance of the methods described herein. In some embodiments, the groove 26, or in combination with the edge 32 and/or rise 34 provides sufficient adherence between the capture portion 16 and the lens 30 to overcome any counter-pressures created within the lens housing 54 (e.g., drainage or travel forces or the adhesive pressure between the lens and the ribs 82, lens base 70, and/or plug 74). Further, the groove 26, edge 32 and/or rise 34 may aid in securing engagement with the con act lens 30 so that the contact lens 30 does not unintentionally become disengaged during use. As will be described infra, the contact lens tool 12 may be used to engage a contact tens 30 housed within a lens housing 54, or, alternatively, the contact lens 30 may be engaged by the contact lens tool 12 independently of a lens housing 54.

By using a contact lens tool 12 to engage a contact lens 30 and place the contact lens 30 onto the eye, the user advantageously is not required to touch the contact lens 30 or contact lens solution 96, thereby reducing the chance of introducing foreign matter or residue to the contact lens 30 or eye. In fact, because the contact lens 30 extends away from the contact lens tool 12 when engaged by the embodiments of the tool 12—see FIG. 3—placement of the contact lens 30 onto the eye does not require the tool 12 to contact the eye either. Further, at least a portion of the contact lens tool 12 and/or the capture portion 16 may be made of soft or flexible material, so that any contact with the eye has less of a risk of damaging the eye.

Figures 4A, 4B, 4C:
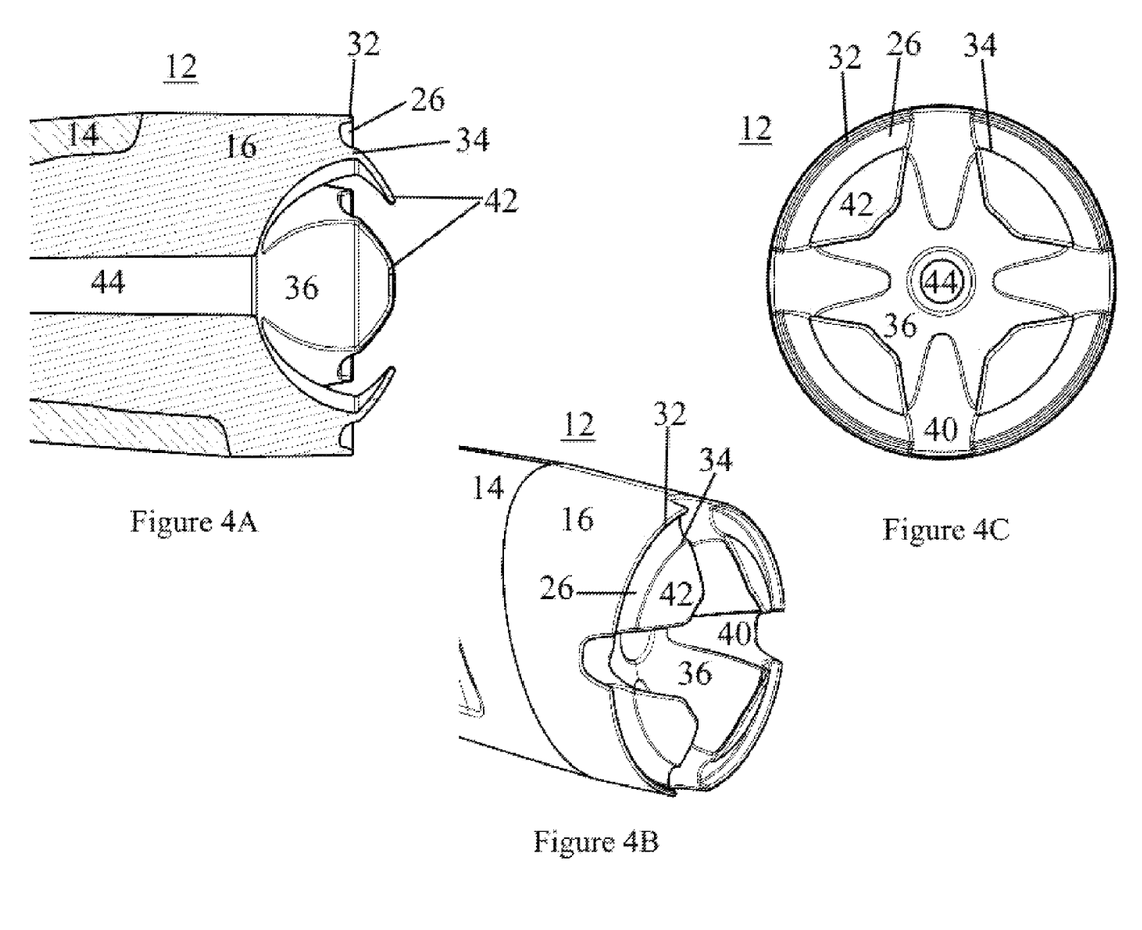
FIG. 4A is a cross-section view of the contact lens tool including wings according to one or more embodiments of the present invention.
FIG. 4B is a perspective view of the contact lens tool including wings according to one or more embodiments of the present invention.
FIG. 4C is an end view of the contact lens tool including wings according to one or more embodiments of the present invention.

According to at least one embodiment, the capture portion 16 may further define at least one cleft 40 and/or wing 42. For example, the capture portion 16 may include at least two clefts 40 positioned opposite from each other and extending centrally through the groove 26 to the cavity 36. In the embodiments of FIGS. 2A and 4A-4C, two pairs of clefts 40 are defined, with each cleft 40 of each pair positioned opposite the other cleft 40 of the same pair. The shape of the cleft 40 may extend within the cavity 36 from the outer edge 32, as depicted in FIG. 4C.

According to at least one embodiment, the capture portion 16 may further define at least one wing 42 for supporting the contact lens 30 when the contact lens 30 is engaged with the contact lens toot 12. The additional frictional contact between the contact tens tool 12 and the contact lens 30 by any wing(s) 42 aids the groove 26 in preventing displacement or deformation of the contact lens 30 when in storage within the contact lens tool kit 10, when the liquid solution 96 is drained, and/or when the contact lens 30 is being placed on the eye by the contact lens tool 12. At least one wing 42 may be advantageous when the contact lens tool 12 is being used with thinner contact lenses 30 by offering greater support and frictional contact to the contact lens 30—a thinner contact lens 30 has an increased probability of deforming or displacing when in storage or use.

In the embodiments of FIGS. 4A-4C, four wings 42 are defined by the capture portion 16. In some embodiments, each wing 42 extends centrally and away from the interior rise 34 of the groove 26. When clefts are defined by the capture portion 16, at least one wing 42 may be positioned between the clefts 40. Further, each wing 42 may be shaped for contouring the contact lens 30 when the contact lens 30 is engaged by the contact lens tool 12. In some embodiments, at least one wing 42 may substantially form an isosceles trapezoid shape, a longest side of the wing 42 being proximal to the rise 34 and a shortest side of the wing 42 being farthest from the rise 34.

As one skilled in the art would realize, numerous configurations of cleft(s) 40 and wing(s) 42 may be incorporated into the structure of the capture portion 16 of the contact lens tool 12. For example, a single wing 42 may be defined by the capture portion 16, the single wing 42 being shaped like a convex cavity 36 and having one or more pores located thereon for fluid flow therethrough. Various porous designs may be provided. Further, any cleft(s) 40 and/or wing(s) 42 may be made of varying materials of a wide range of thicknesses, whether rigid or soft, coarse or smooth, permeable or non-permeable. As noted supra, flexibility of any wing(s) 42 may help to reduce potential damage or irritation to the eye during placement of a contact lens 30 using the contact lens toot 12. Similarly, thinner wings 42 may be desirable to minimize abrasive contact with the eye when the contact lens tool 12 is in use.

According to at least one embodiment, the capture portion 16 may be shaped to invert the contact lens 30 upon engagement therewith. For example, the rise 34, wing(s) 42 and/or a convex cavity 36 may work in conjunction with a lens housing 54 to invert the lens 30 and engage the contact lens tool 12 with the lens 30.

According to some embodiments, the capture portion 16 further defines an aperture 44 extending centrally along a length thereof for permitting fluid flow therethrough. For example, the aperture 44 may extend from the cavity 36 along the length of the contact lens tool 12 to an opening 46 for permitting fluid flow from the cavity 36 to the opening 46 and vise versa. Some embodiments of the aperture 44 include the added advantage of a user being able to visually align placement of the contact lens 30 during use; this visual alignment encourages consistent and accurate placement of the contact lens 30 onto the eye by the contact lens tool 12.

According to at least one embodiment of the present invention, the contact lens tool 12 may include a handle portion 14 at least partially covering the exterior of the capture portion 16. The handle portion 14 may be securely coupled or releasably engaged to the capture portion 16. Further, the handle portion 14 may define an opening 46 engaged with the the capture portion 16 or the aperture 44 of the capture portion 16 for permitting fluid flow through the opening 46 and/or the aperture 44. As one skilled in the art would appreciate, the handle portion 14 may include grooves, coarse treatments, and/or gripping elements on its surface for providing improved handling of the contact lens tool 12 during use. Further the handle may be made of rigid and/or soft materials. For example, the handle 14 may include missing portions, thereby exposing the capture portion 16 underneath, the capture portion extending through the exposed portions for providing a gripping element for the user. In the embodiment of FIG. 2A, an elongated indent is defined by the handle 14 for providing greater accuracy during manipulation of the contact lens tool 12. In the embodiment of FIG. 2B, two smaller indentions are defined by the handle 14 for improved handling of the contact lens tool.

According to embodiments, the tool housing 52 may define a tool exterior 56 and a tool base 60 positioned on one end of the tool exterior 56. The tool base 60 may define a pole 62 extending within the tool exterior 56 for selectively engaging the contact lens tool 12. The pole 62 may engage the aperture 44 and/or opening 46. Engagement of the aperture 44 and/or opening 46 by the pole 62 may seal the aperture 44 and/or opening 46 such that fluid flow is not permitted therethrough.

The tool housing 52 may further define at least one protrusion 94 extending within the tool exterior 56 for supporting the contact lens tool 12 when engaged with the tool housing 52. For example, as depicted in FIG. 1, an annular protrusion 94 may extend from the tool base 60, thereby providing a recess in which the contact lens tool 12 may be housed and supported. By supporting the contact lens tool 12, the at least one protrusion 94 may help maintain the correct positioning of the contact lens tool 12 relative to the contact lens 30, a ledge 84, and/or the pole 60.

Figures 5A, 5B, 5C:
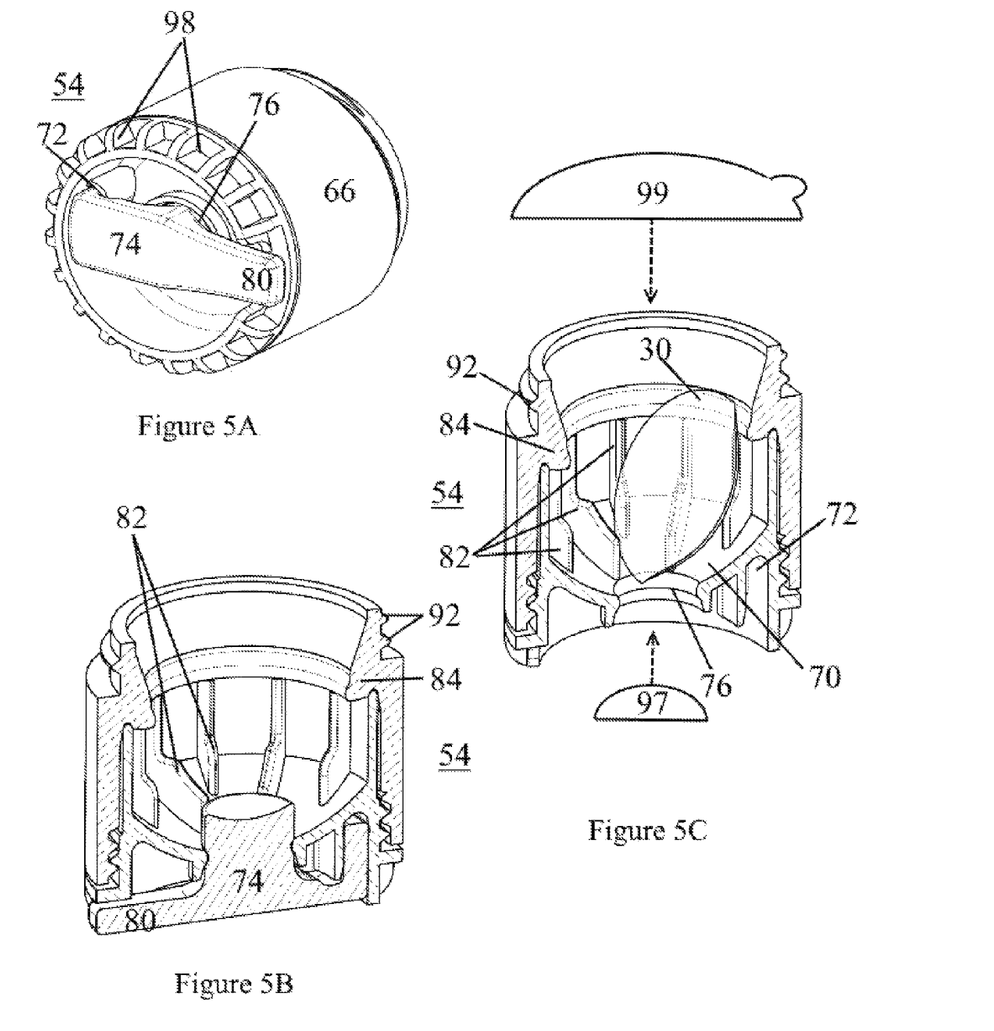
FIG. 5A is a perspective view of the lens housing according to one or more embodiments of the present invention.
FIG. 5B is a cross-section view of the lens housing according to one or more embodiments of the present invention.
FIG. 5C is a cross-section view of the lens housing and contact lens according to one or more embodiments of the present invention.
Figure 6:
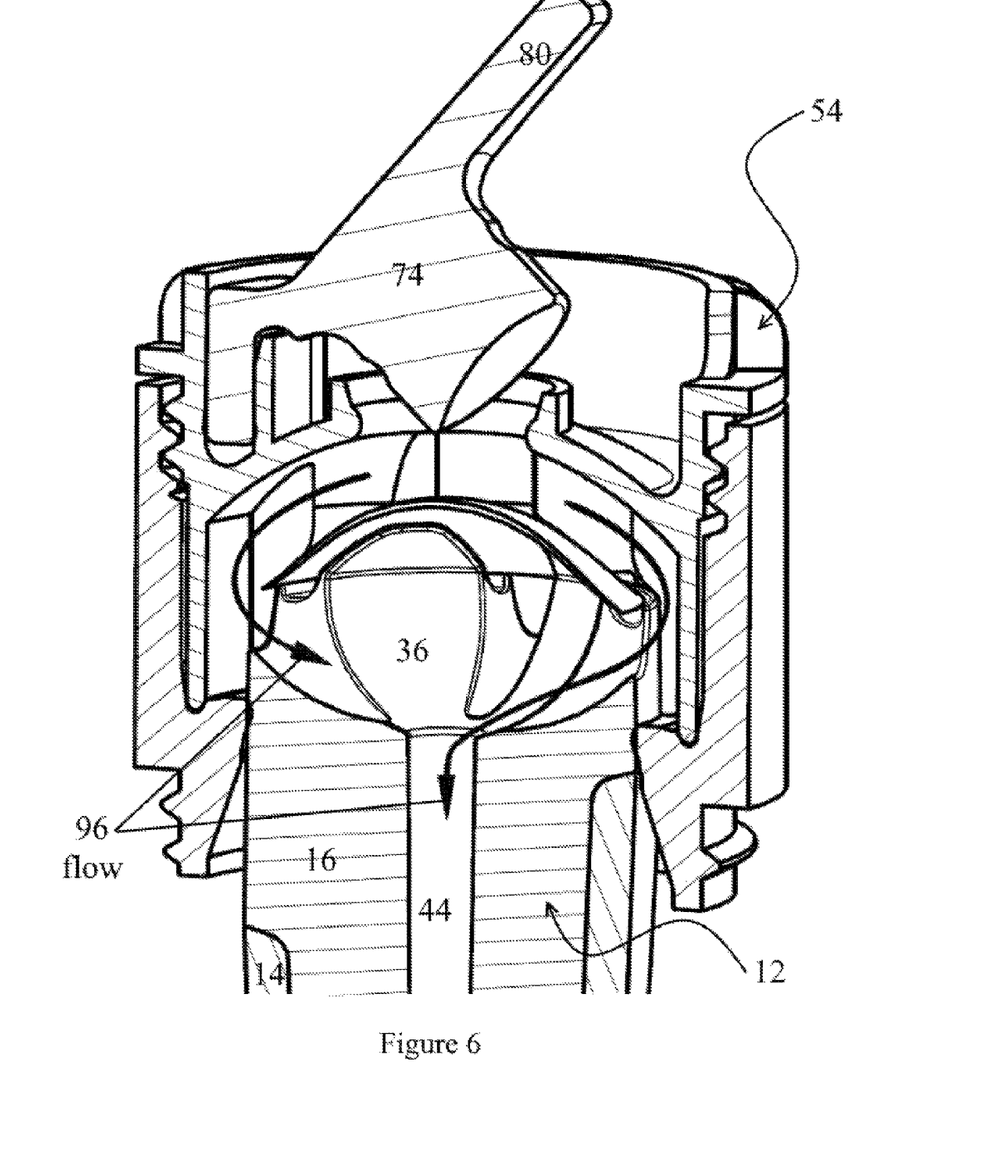
FIG. 6 is a cross-section of the contact leas tool kit in operation according to one or more embodiments of the present invention.

In FIGS. 5A-5C, a lens housing 54 defining a lens base 70 on one end is depicted. The lens base depicted in FIG. 5A includes gripping features 98 on the surface to aid the user in manipulating the lens housing 54. The cross section view of FIG. 5B depicts a lens housing including a plug 74 for releasing fluid therein. The plug 74 may be releasably engaged with the lens housing 54 or may be securely coupled to the lens housing 54 or both. For example, a plug aperture 76 may be defined by the lens housing 54 for coupling the plug 74 to the lens housing 54. Additionally, plug aperture 76 may be defined by the lens housing 54 for selectively engaging the plug 74. Additionally, the plug may define a plug lip 80 for permitting a user to easily manipulate the plug 74 to, for example, selectively engaging the plug 74 with the plug aperture 76. As depicted in FIGS. 5A and 5B, the plug 74 may have a substantially flat surface so that, when coupled and/or engaged with the lens housing 54, the lens housing may lay flat on a surface in contact with the lens base 70 end of the lens housing 54.

In embodiments where the plug 74 is selectively engaged with a plug aperture 76, the plug may extend a distance past the plug aperture 76 of the lens base for supporting a contact lens 30 when housed within the lens housing 54. Further, the portion of the plug 74 extending through the plug aperture 76 may be shaped to conform to the shape of a contact lens 30. The surface of the plug 74 supporting the contact lens 30 may include surface indentations or be coarse in nature or involve other physical features in order to minimize the surface tension between the contact lens 30 and plug 74. For example, the plug 74 may include clefts similar to the capture portion 16 and/or may include an annular rise similar to the capture portion 16, where the interior portion of the surface of the plug 74 has a greater concavity than the tens 30 such that only the annular rise is in contact with the lens 30. In most embodiments of the plug 74, when the plug is disengaged from the aperture 76 of the lens housing 54, the disengagement reduces the adhesion between the contact lens 30 and the lens housing 54, thereby permitting easier removal of the contact lens 30 by the lens tool 12. For example, a plug 74 supporting a contact lens 30 will create adhesion between the two when in contact; disengagement of the plug 74 removes these adhesive properties.

The lens base 70 may define least one rib 82 for receiving and/or supporting the contact lens. For example, the lens base 70 may define a plurality of ribs 82 extending centrally within the lens housing 54 for receiving the contact lens 30, as depicted in FIGS. 5B and 5C. As one skilled in the art would appreciate, numerous rib 82 configurations are available to serve at least one purpose of receiving a contact lens 30, supporting the contact lens 30 to prevent deformation or improper settlement of the contact lens 30, minimizing surface tension between the contact lens 30 and any rib(s) 82 for easier removal from the lens housing, and suspending the contact lens 30 in a liquid solution 96 so that foreign objects may settle without contact with the contact lens 30. One example may include ribs 82 shaped to conform to the shape of the contact lens 30. Another embodiment may include the ribs 82 working in conjunction with the plug 74. Yet another embodiment may include at least one rib 82 extending across the entire width of the lens base 70, such that each rib 82 engages the lens 30 through a finite number of contact points.

As depicted in FIG. 5C, the lens housing 54 may define a lens base 20 and further include a drain seal 97 and/or housing seal 99. The lens housing 54 may be capable of storing a contact lens 30 suspended in a liquid solution 96 therein. A lens housing 54 having a drain seal 97 and/or housing seal 99 may additional include any of the features described herein, alone or in combination, such as various configurations of ribs 82, a ledge 84, and gripping features 98. The drain seal 97 and/or housing seal 99 may be a flexible membrane, and may be removable and/or frangible. A contact lens tool kit 10 having a lens housing 54 including a housing seal 99 may also include a tool housing 52 having a plug 74 and/or a tool 12 having a plug 74. The embodiments where the lens housing 54 includes a housing seal 99 may be used to package and store one-time-use contact lenses 30. Drainage of the liquid solution 96 from the lens housing 54 may be performed using the drain seal 97, a plug 74 engaged and/or coupled with the tool 12, and/or a plug 74 engaged and/or coupled with a tool housing 52. The method of using a lens housing 54 with a drain seal 97 and/or housing seal 99 in conjunction with other components of the contact lens tool kit 10 is further described infra.

In other embodiments, the lens housing 54 may be capable of engagement with a capture portion 16 of a lens tool 12 such that the engagement is impermeable to fluid flow. In such an embodiment, the liquid solution 96 and lens 30 may be stored in the lens housing 54 while engaged with the capture portion 16. Disengagement of the capture portion 16 from the lens housing 54, whether by direct disengagement of the tool 12 or by indirect disengagement through selective engagement of a handle portion 14 with the capture portion 16 of the tool 12, thereby removes the lens 30 from the lens housing 54. In one embodiment, the engagement of the handle 14 with the capture portion 16 may enlarge an aperture 44 in the capture portion 16 or break a frangible seal on the aperture 44 of the capture portion, thereby aligning the aperture 44 with the opening 46 of the handle for draining the liquid solution 96 from the lens housing 44. Alternatively, a drain seal 97 located on the lens housing 44 may be removed or broken for draining.

According to some embodiments, the lens housing 54 may further define a ledge 84 extending centrally for supporting engagement of the contact tens tool 12 when the lens housing 54 and tool housing 52 are engaged or when the contact lens tool 12 is attempting to engage the contact lens 30 received by the lens housing 54. As depicted in FIGS. 5B and 5C, the ledge 84 may be shaped with a taper and/or curve to provide varying engagement with the contact lens tool 12.

For manufacturing purposes, the lens housing 54 may be constructed using two components that are securely engaged with each other. The lens housing may be impermeable to fluids or liquid fluids. The tool housing may include tool housing engagements 64. The lens housing may include lens housing engagements 92. Both engagements 64, 92 may be configured so that fluids or liquid fluids may not flow therebetween when engaged with each other. Engagement of the tool housing 52 with the lens housing 54 may be impermeable to fluids or liquid fluids.

According to at least one embodiment, a method of engaging a contact lens 30 with a contact lens tool 12 is provided. The method may include the step of providing a contact lens tool kit 10 according to any embodiments described herein. For example, the contact lens tool kit 10 may include a tool housing 52, a lens housing 54 and a contact lens tool 12. Alternatively, the method may require a lens housing 54 and a contact lens tool 12, without the need for a tool housing 52. A step of the method may include pouring a liquid solution 96 into a lens housing 54. A contact lens 30 may then be inverted and placed in the liquid solution 96 of the lens housing 54. Alternatively, the lens 30 may be placed in the liquid solution 96 without being inverted, allowing for a contact lens tool 12 to invert the contact lens 30 upon engagement. The lens housing 54 may be any embodiment described herein or, alternatively, may be a contact storage case traditionally used in the prior art. A step of the method may include inserting the contact lens tool 12 into the lens housing 54, thereby engaging the contact lens tool 12 with the contact lens 30 and the lens housing 54. FIG. 3 depicts the contact lens tool 12 in engagement with the contact lens 30.

According to some embodiments, a method may include providing a lens housing 54 with at least one lens seal 99. The lens housing 54 may contain therein a contact lens 30 suspended in liquid solution 96. The contact lens 30 may be either inverted or not-inverted when in suspension. The method may include removing or breaking a seal 99 from the lens housing 54. The seal 99 may be removed for subsequent engagement of the lens housing 54 with either a lens tool 12 or tool housing 52. Alternatively, engagement of the lens housing 54 with the lens tool 12 or tool housing 52 may cause the lens seal 99 to break, thereby allowing fluid flow therebetween. Once the lens housing 54 is engaged to either the lens tool 12, the tool housing 52 or both, a second lens seal 99 may be removed or broken for draining the liquid solution 96 from the lens housing 54. Alternatively, a plug 74 positioned on the tool 12 and/or tool housing 52 may be disengaged for draining the liquid solution 96.

In at least one embodiment, a method may include the step of a tool 12 engaging a lens housing 54, thereby breaking a frangible seal 99 of the lens housing 54 engaging a contact lens 30 housed therein. A plug 74 may then be removed from the aperture 44 of the tool 12 for draining the liquid solution 96 in which the contact tens 30 is suspended. In one embodiment, the lens housing 54 defines at least one rib 82 for supporting a non-inverted tens 30 such that engagement of the lens housing 54 with the tool 12 involves at least one wing 42 inverting the contact lens 30 with support of the at least one rib 82.

As described supra, various features of the contact lens tool kit 10 may aid in providing alignment and support to the contact lens tool 12 for proper engagement with the contact lens 30. For example, the interaction of the tool 12 with the ledge 84 may help ensure that the toot 12 aligns with the contact lens 30. Additionally, the ribs 82 and/or plug 64 may help ensure that the contact lens 30 is properly positioned for engagement within the lens housing 54. When using the tool housing 52 as well, the pole 62 and/or the protrusion 94 may help ensure proper positioning.

According to at least one embodiment, the method may include providing a toot housing 52, wherein the step of inserting the contact lens tool 12 into the lens housing 54 may involve engaging the tool housing 52 with the lens housing 54. In method embodiments wherein both a lens housing 54 housing a contact lens 30 and a toot housing 52 housing a lens tool 12 are involved, engagement of the lens housing 54 with the tool housing 52 causes engagement of the lens tool 12 with the contact lens 30. When the toot housing 52 and tens housing 54 are disengaged, the lens tool 12 may be removed with the contact lens 30 engaged thereto. After the contact lens 30 is engaged by the contact lens toot 12, in any embodiment described herein, a user may then conveniently insert the contact lens 30 onto the eye. 19.

According to at least one embodiment, a lens housing 54 is provided and includes a plug 64. The method may include disengaging the plug 64 from the lens housing 54, thereby releasing the liquid solution 96 from the lens housing. Subsequently, the contact lens tool 12 may be removed from the lens housing 54, thereby removing the contact lens 30 engaged to the contact lens toot 12. Alternatively, before disengaging the plug 64, the method may also include disengaging the tool housing 52 from the lens housing 54 such that the contact lens tool 12 remains engaged with the lens housing 54.

According to some embodiments, a lens 30 is stored within a liquid solution 96 within a tens housing 54. The lens housing 54 may be engaged to both a toot housing 52 and a contact lens tool 12. The tool housing 52 may be disengaged from the lens housing 54, the lens tool 12 remaining engaged with the lens housing 54. The contact lens 30 may remain suspended in the liquid solution 96, which remains in the lens housing 52. The lens housing 52 and the contact lens toot 12 may together be lifted, inverted, and relocated within risk of the liquid solution 96 escaping the confines of the lens housing 52 and/or the aperture 44 of the tool 12. Due to the surface tension of the liquid solution 96 in the aperture 44, the liquid solution 96 does not flow even when the aperture 44 and/or opening 46 is directed downward, with the contact lens 30 and solution 96 primarily positioned above the aperture 44 and/or opening 46. When positioned so, the plug 64 may be disengaged from the tens housing 44 and the solution 96 may flow through the aperture 44 and/or opening 46, thereby draining the solution 96 from the lens housing 44. Once the solution has been drained, the contact lens tool 12 may be disengaged from the lens housing 44, with the lens 30 engaged to the tool 12 for placement on the eye.

As described supra, several features of the present invention may be included to aid either the flow of the solution 96 during draining and/or the flow of air through the tool 12 during placement. For example, the aperture 44 and/or opening 46 may have a diameter or width necessary for maintaining a desired surface tension on the solution 96 contained therein. Further, the aperture 44 and/or opening 46 permits liquid flow during drainage and air flow during placement of the contact lens on the eye. Notably, when the capture portion 16 is inserted into the lens housing 54, the liquid solution 96 is displaced and therefore displaces gases contained within the lens housing 54 without the lens housing 54. In some embodiments, the engagement of the lens tool 12 with the lens housing 54 causes any gas within the lens housing to displace without the lens housing 54, thereby creating a gas-free, fluid-only volume within the lens housing 54 for storage of the contact lens 30. Additionally, the ribs 82, plug 74, plug aperture 76, cavity 36, cleft(s) 40, and/or wing(s) 42 may also work along, or in combination to provide liquid and air flows during drainage, engagement, inversion and/or placement.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

The invention claimed is:

1. A contact lens tool kit comprising:
a contact lens tool including a capture portion having an annular groove; and
a lens housing for receiving a contact lens, the lens housing engageable with the contact lens tool,
wherein engagement of the contact lens tool and the lens housing permits reception of the contact lens by the annular groove of the contact lens tool.

2. The contact lens tool kit of claim 1, further comprising:
a tool housing engaged with the contact lens tool,
wherein engagement of the contact lens tool and the lens housing creates an engagement between the tool housing and lens housing which is impermeable to fluid flow.

3. The contact lens tool kit of claim 1, wherein the capture portion further defines a hemispherical cavity positioned internally proximal to the groove, and wherein the cavity is either concave or convex.

4. The contact lens tool kit of claim 3, wherein the capture portion further defines at least two clefts positioned opposite from each other and extending centrally through the groove to the cavity.

5. The contact lens tool kit of claim 4, further comprising at least two wings, each of the wings:
extending centrally and away from the interior rise of the groove;
positioned between the clefts for supporting the contact lens; and
shaped for contouring the contact lens when inverted.

6. The contact lens tool kit of claim 4, wherein the capture portion defines an aperture extending centrally from the cavity along the length of the contact lens tool to an opening for permitting fluid flow therethrough.

7. The contact lens tool kit of claim 1, wherein an exterior of the capture portion is partially covered by a handle portion coupled thereto.

8. The contact lens tool kit of claim 7, wherein the handle portion defines an opening engaged with an aperture extending from the cavity of the capture portion for permitting fluid flow therethrough.

9. The contact lens tool kit of claim 1, wherein engagement of the tool housing with the lens housing is impermeable to fluids.

10. The contact lens tool kit of claim 2, wherein the tool housing defines:
an tool exterior with a tool base positioned on one end of the tool exterior; and
the tool base defining a pole extending within the tool exterior for selectively engaging the contact lens tool.

11. The contact lens tool kit of claim 10, wherein the tool housing further defines at least one protrusion extending within the tool exterior for supporting the contact lens tool when engaged with the tool housing.

12. The contact lens tool kit of claim 1, wherein the lens housing defines a lens base selectively engaged with a plug for releasing fluid therein.

13. The contact lens tool kit of claim 12, wherein the lens base defines a plurality of ribs extending centrally within the lens housing for receiving the contact lens.

14. The contact lens tool kit of claim 12, wherein the lens housing further defines a ledge extending centrally for supporting the contact lens tool when the lens housing and tool housing are engaged.

15. The contact lens tool kit of claim 1, further comprising a handle for engaging the capture portion of the contact lens tool and for disengaging the contact lens tool from the lens housing.

16. The contact lens tool kit of claim 15, wherein the handle includes an opening and a plug or seal engaged with the opening for draining when the plug or seal is disengaged from the opening.

17. A method of engaging a contact lens with a contact lens tool comprising:
providing the contact lens tool kit comprising:
a contact lens tool including a capture portion defining an annular groove for receiving the contact lens; and
a lens housing including a liquid solution and the contact lens therein;
inserting the contact lens tool into the lens housing, thereby engaging the contact lens tool with the contact lens and the lens housing.

18. The method of claim 17, further comprising:
disengaging a plug from the lens housing, thereby releasing the liquid solution; and
removing the contact lens tool from the lens housing, thereby removing the contact lens engaged to the contact lens tool.

19. The method of claim 17, further comprising:
providing a tool housing,
wherein the step of inserting the contact lens tool into the lens housing involves engaging the tool housing with the lens housing.

20. The method of claim 19, further comprising:
disengaging the tool housing from the lens housing such that the contact lens tool remains engaged with the lens housing;
disengaging a plug from the lens housing, thereby releasing the liquid solution; and
removing the contact lens tool from the lens housing, thereby removing the contact lens.

* * * * *